(12) United States Patent
Stearns et al.

(10) Patent No.: US 9,808,578 B2
(45) Date of Patent: Nov. 7, 2017

(54) DELIVERY SYSTEM FOR INJECTIONS THROUGHOUT ZONE OF BODY

(71) Applicant: Gabriel Institute, Inc., Houston, TX (US)

(72) Inventors: Stanley D. Stearns, Houston, TX (US); H. Max Loy, Jr., Houston, TX (US); Donald G. Davis, Baton Rouge, LA (US)

(73) Assignee: Gabriel Institute, Inc., Houston, TX (US)

( * ) Notice: Subject to any disclaimer, the term of this patent is extended or adjusted under 35 U.S.C. 154(b) by 462 days.

(21) Appl. No.: 14/679,756

(22) Filed: Apr. 6, 2015

(65) Prior Publication Data

US 2015/0224260 A1 Aug. 13, 2015

Related U.S. Application Data

(63) Continuation-in-part of application No. 13/298,742, filed on Nov. 17, 2011, now Pat. No. 9,022,987, (Continued)

(51) Int. Cl.
*A61M 5/00* (2006.01)
*A61M 5/28* (2006.01)
(Continued)

(52) U.S. Cl.
CPC ............ *A61M 5/284* (2013.01); *A61M 5/172* (2013.01); *A61M 5/1785* (2013.01); (Continued)

(58) Field of Classification Search
CPC .... A61M 5/284; A61M 5/172; A61M 5/1785; A61M 5/2035; A61M 5/232; A61M 5/46; A61M 5/484
(Continued)

(56) References Cited

U.S. PATENT DOCUMENTS

| 984,037 A | 2/1911 | Sheets |
|---|---|---|
| 4,392,859 A | 7/1983 | Dent |

(Continued)

OTHER PUBLICATIONS

Linda Sholl, International Preliminary Report on Patentability—PCT/US12/60818, dated Oct. 16, 2013, 6 pages, United States Patent and Trademark Office, Alexandria, Virginia USA.
(Continued)

*Primary Examiner* — Edelmira Bosques
(74) *Attorney, Agent, or Firm* — Crain, Caton & James; James E. Hudson III (57) ABSTRACT

A dispensing device which disperses medicate through a needle across a zone within a body. The device includes a needle which is, during use, becomes encapsulated within a tubular needle-receiving member, a reservoir in fluid communication with the needle, positioned within the housing, and in communication with the needle, a second reservoir, a reservoir-connecting conduit in communication with the reservoir, a fluid drive in communication with the fluid in the second reservoir and in communication with the reservoir-connecting conduit, and a linear drive attached to the needle or to the needle-receiving member. The fluid drive impel fluids from the second reservoir to the reservoir-connecting conduit and thus drives the therapeutic agent from the reservoir during the linear displacement of the needle towards the housing. Fluid communication from the therapeutic agent reservoir to the needle is maintained by the tubing during operation of the linear drive.

2 Claims, 6 Drawing Sheets

Related U.S. Application Data which is a continuation-in-part of application No. 12/276,637, filed on Nov. 24, 2008, now Pat. No. 8,529,516.

(60) Provisional application No. 61/078,674, filed on Jul. 7, 2008.

(51) Int. Cl.
| | | |
|---|---|---|
| *A61M 5/48* | (2006.01) | |
| *A61M 5/172* | (2006.01) | |
| *A61M 5/178* | (2006.01) | |
| *A61M 5/20* | (2006.01) | |
| *A61M 5/32* | (2006.01) | |
| *A61M 5/46* | (2006.01) | |
| A61M 5/168 | (2006.01) | |

(52) U.S. Cl.
CPC ............ *A61M 5/2053* (2013.01); *A61M 5/32* (2013.01); *A61M 5/46* (2013.01); *A61M 5/484* (2013.01); *A61M 5/16886* (2013.01); *A61M 2202/049* (2013.01); *A61M 2205/3334* (2013.01); *A61M 2206/20* (2013.01)

(58) Field of Classification Search
USPC ........................................................ 604/187
See application file for complete search history.

(56) References Cited

U.S. PATENT DOCUMENTS

| | | | |
|---|---|---|---|
| 5,125,414 | A | 6/1992 | Dysarz |
| 5,772,661 | A | 6/1998 | Michelson |
| 5,891,105 | A | 4/1999 | Mahurkar |
| 6,039,127 | A | 3/2000 | Myers |
| 6,056,716 | A | 5/2000 | D'Antonio et al. |
| 6,645,181 | B1 | 11/2003 | Lavi et al. |
| 8,529,516 | B2 | 9/2013 | Stearns |
| 8,828,001 | B2 | 9/2014 | Stearns et al. |
| 8,900,234 | B2 | 12/2014 | Stearns et al. |
| 2002/0068907 | A1 | 6/2002 | Dysarz |
| 2004/0050864 | A1 | 3/2004 | Stradella |
| 2005/0236189 | A1 | 10/2005 | Rankin |
| 2009/0228014 | A1 | 9/2009 | Stearns et al. |
| 2010/0004604 | A1 | 1/2010 | Stearns |
| 2010/0049140 | A1 | 2/2010 | Marsh et al. |
| 2010/0185152 | A1 | 7/2010 | Larsen et al. |
| 2010/0196268 | A1 | 8/2010 | Frank et al. |
| 2010/0256644 | A1 | 10/2010 | Stearns et al. |
| 2011/0238009 | A1 | 9/2011 | Meron et al. |
| 2012/0065618 | A1 | 3/2012 | Stearns et al. |
| 2012/0251442 | A1 | 10/2012 | Frank et al. |
| 2012/0259340 | A1 | 10/2012 | Stearns et al. |

OTHER PUBLICATIONS

Blaine R. Copen Heaver, International Search Report—PCT/US2012/060818, dated Jan. 2, 2013, 2 pages, USPTO as International Searching Authority, Alexandria, Virginia, US.

Blaine R. Copen Heaver, Written Opinion of the International Searching Authority—PCT/US2012/060818, dated Jan. 2, 2013, 4 pages, USPTO as International Searching Authority, Alexandria, Virginia, US.

Linda Sholl, Notification of transmittal of International Preliminary Report on Patentability—PCT/US09/49669, dated Jul. 27, 2010, 1 page, United States Patent and Trademark Office as Examining Authority, Alexandria, Virginia, USA.

Linda Sholl, International Preliminary Report on Patentability—PCT/US09/49669, dated Jul. 27, 2010, 6 pages, United States Patent and Trademark Office as Examining Authority, Alexandria, Virginia, USA.

Webster's II New College Dictionary, ps. 19, 72, 1995, 4 pages, Houghton Mifflin Company, Boston, Massachusetts, USA.

Lee W. Young, International Preliminary Report on Patentability—PCT/US08/02026, dated Nov. 8, 2010, 3 pages, United States Patent and Trademark Office as International Search Authority, Alexandria, Virginia, US.

Nicholas W. Woodall, Notice of Allowance—U.S. Appl. No. 12/437,910, dated Jun. 11, 2012, 7 pages, United States Patent and Trademark Office, Alexandria, Virginia, US.

Michael T. Schaper, Office Action—U.S. Appl. No. 12/064,276, dated Apr. 24, 2014, 12 pages, United States Patent and Trademark Office, Alexandria, Virginia, US.

Thomas Dunn, Notification of Transmittal of International Preliminary Report on Patentability—PCT/US08/054085, dated Aug. 10, 2009, 2 pages, United States Patent and Trademark Office as International Preliminary Examining Authority, Alexandria, Virginia, US.

Thomas Dunn, International Preliminary Report on Patentability—PCT/US08/054085, dated Aug. 7, 2009, 7 pages, United States Patent and Trademark Office as International Preliminary Examining Authority, Alexandria, Virginia, US.

James E. Hudson III, Response to Non-Final Rejection—U.S. Appl. No. 12/064,276, dated May 12, 2014, 12 pages, Crain, Caton & James, P.C., Houston, Texas US.

DELIVERY SYSTEM FOR INJECTIONS THROUGHOUT ZONE OF BODY

CROSS REFERENCE TO RELATED APPLICATIONS

This application claims the benefit of U.S. Provisional Patent Application No. 61/078,674 entitled, "Syringe for injection through zone of body" filed on Jul. 7, 2008 in the United States Patent and Trademark Office and is a continuation-in-part of U.S. patent application Ser. No. 12/276,637, Syringe for injection through zone of body, filed Nov. 24, 2008, now U.S. Pat. No. 8,529,516 issued Sep. 10, 2013, and is a continuation-in-part of U.S. patent application Ser. No. 13/298,742, Syringe for injection through zone of body, filed Nov. 7, 2011.

BACKGROUND OF THE INVENTION

Field of the Invention

The present invention relates to an apparatus for delivery of medical treatment by injections throughout a zone of a body. More particularly, the invention relates to automated devices and systems for the delivery and injection of therapeutic agents, solutions or injectates throughout or at locations across a portion of bodily tissue. Additionally, the invention relates to methods of delivering and injecting a solution across a target site within the body for the treatment of that target site.

Description of the Related Art

Hypodermic syringes are widely used in the medical field for administering medicaments. Generally, hypodermic syringes include a needle having a sharpened distal point for penetrating vial stoppers or patient's body. The needle is attached either fixedly or removably to a syringe barrel. In operation, these syringes provide the means to deliver medicaments to a single specific location in the body. In operation, the plunger is depressed into the barrel and the medicament thus discharged. This system, largely unchanged since the invention of the syringe, contemplates delivery of the therapeutic agent at a single location wherein the effect of the therapeutic agent is transmitted through adjacent cells. Problematically, when the therapeutic agent is intended to act against a collection of cells, its effectiveness is reduced and/or delayed by such transmission, even though the overall distance from one side of the collection of cells to the other may be quite small. Practitioners have attempted to overcome this limitation and provide the benefit of a dispersed delivery by simultaneously depressing the syringe plunger with the thumb while also withdrawing the syringe. However, this technique is difficult to learn and is ineffective to properly deliver the therapeutic agent to the desired location in the desired quantities, particularly when the desired location has defined boundaries, such as a tumor.

Additionally, delivery systems have been constructed to provide delivery of a therapeutic agent with an automated system. However, these systems either suffer the same shortcomings as conventional syringes or suffer from the necessity to provide the therapeutic agent into a dynamic system, such as blood flow, which results in the undesirable distribution of therapeutic agents throughout the body instead of localized distribution.

Further, when the therapeutic agent poses a danger to care providers, such as in the case radioactive agents, it is desirable to minimize the exposure to the care provider, particularly by limiting the time of exposure to the care provider, by providing a delivery system which inhibits or prevents exposure, and by providing a delivery system which limits the extent of therapeutic agent used.

Further, it has been determined that, particularly in connection with radioactive agents, it is more advantageous to generate within the body a three-dimensional grid of therapeutic agent injections, such that the effective area of each therapeutic agent injection abuts but does not detrimentally overlap the effective area of an adjacent therapeutic agent injection, particularly beneficial where the therapeutic agent contains a radioactive element, and such that the minimum necessary volume of therapeutic agent is used.

There is therefore a need for a delivery system that disburses a therapeutic agent along a path of a collection of cells in a body by automated means.

SUMMARY OF THE INVENTION

It is therefore, a principle object of the present invention to provide a delivery system which disburses a therapeutic agent along the path of a collection of cells in a body based on limited action by the operator.

In particular, a principal object of the present invention is to provide a system utilizing a delivery device which retracts the needle as fluid is dispensed into the body or at locations across a portion of bodily tissue, wherein the fluid is stored in a reservoir and delivered via a pump or separate syringe coordinated with the movement of the retracting needle in a manner wherein the necessary therapeutic agent is delivered. The needle may move in such a fashion as to introduce the fluid with a zero pressure differential while the therapeutic agent is pushed forward, preferably with another fluid. Alternatively, the needle may move is such a fashion as to introduce a metered volume of therapeutic agent at a series of positions. Thus, in the case of introduction of a radioactive agent, the exposure to radiation by the care provider or technician is reduced. The unit may be hand-held or robotic. Thus, fluid is not inaccurately "squirted" from the needle, but rather deposited during retraction of the needle, either as a continuous path or as a series of separated locations. As the needle may be introducing a radioactive therapeutic agent, the needle is ideally encapsulated by a shielding needle-receiving member.

The foregoing advantages are achieved through a device which includes a needle which is, during use, encapsulated within a tubular needle-receiving member, a reservoir adapted to be filled with a therapeutic agent, in fluid communication with the needle, positioned within the housing, and in communication with the needle, a second reservoir, a reservoir-connecting conduit in communication with the therapeutic agent reservoir, a fluid drive in communication with the fluid in the second reservoir and in communication with the reservoir-connecting conduit, and a linear drive attached to the needle or to the needle-receiving member. The therapeutic agent reservoir may be a holding coil or a large barrel.

In one embodiment, the linear drive provides a linear displacement of either the needle or the needle-receiving member at a constant rate so the product of the linear displacement and internal cross-sectional area of the needle determines a volume of displacement and a flow rate and the fluid drive impel fluid from the second reservoir to the a reservoir-connecting conduit, which may be non-therapeutic at the flow rate during the linear displacement and which pushes the therapeutic agent fluid from the therapeutic agent reservoir and into the needle during its retraction from the body.

In another embodiment, the fluid drive is bidirectional and is adapted to impel fluid from the second reservoir to the reservoir-connecting conduit and to drive the therapeutic agent from the therapeutic agent reservoir after the linear displacement of the needle towards the housing while fluid communication from the therapeutic agent reservoir to the needle is maintained by the tubing during operation of the linear drive to provide a linear displacement of the needle towards the housing, or to provide a linear displacement of the needle-receiving member away from the housing.

In operation of first embodiment, a needle having an internal cross-sectional area is driven into the body and then retracted, preferably at a fixed or constant velocity although a control system may be used to vary the rate between depositions if a therapeutic agent is to be positioned at discrete locations throughout the body, by a linear drive into a housing including a needle receiving member so that the needle is encapsulated during retraction. The product of the velocity of retraction and the cross sectional area of the needle provide a flow rate. During retraction, fluid from a second reservoir is impelled by a pump through a reservoir-connecting conduit to a therapeutic agent reservoir, preferably a coil of tubing, containing the therapeutic agent at the determined flow rate. By virtue of the small cross sectional area and diameter of the tubing comprising the therapeutic agent reservoir, the therapeutic agent is displaced without mixing with the fluid and is ejected from the needle at predetermined flow rate, resulting in a zero pressure differential during injection, while the needle is being retracted.

Thus, particularly small volumes of an therapeutic agent may be repeatedly deposited with a high degree of accuracy, which provides an improvement over any human attempt to do so. This may be particularly important when the therapeutic agent contains a radioactive element.

The foregoing and other objectives, features and advantages of the invention will be more readily understood upon consideration of the following detailed description of the invention, taken in conjunction with the accompanying drawings.

BRIEF DESCRIPTION OF THE DRAWINGS

So that the manner in which the described features, advantages and objects of the invention, as well as others which will become apparent, are attained and can be understood in detail, more particular description of the invention briefly summarized above may be had by reference to the embodiments thereof that are illustrated in the drawings, which drawings form a part of this specification. It is to be noted, however, that the appended drawings illustrate only a typical preferred embodiment of the invention and are therefore not to be considered limiting of its scope as the invention may admit to other equally effective embodiments.

DETAILED DESCRIPTION OF THE PREFERRED EMBODIMENT

The present invention involves an improvement of delivery of one or more injections throughout a zone of a body. More particularly, the invention involves a syringe for the delivery and injection of therapeutic agents, solutions or injectates, whether over a portion of bodily tissue as a continuous path throughout a zone of the body, rather than in a single location or as a series of separated locations throughout a zone of the body, resulting in periodic injection, whether the period between injections is essentially zero (resulting in essentially continuous flow) or some longer time frame. The therapeutic agent may be a fluid containing a radioactive element, a non-radioactive chemical treatment, a gel or even a paste.

Ideally, the invention provides an injection system which distributes therapeutic agent along a line of injection during removal of the needle from the body. The system includes a needle, a housing with a tubular needle-receiving member, a therapeutic agent reservoir, a second reservoir, a reservoir-connecting conduit, a fluid drive, a computer, and a linear drive.

Figure 1:
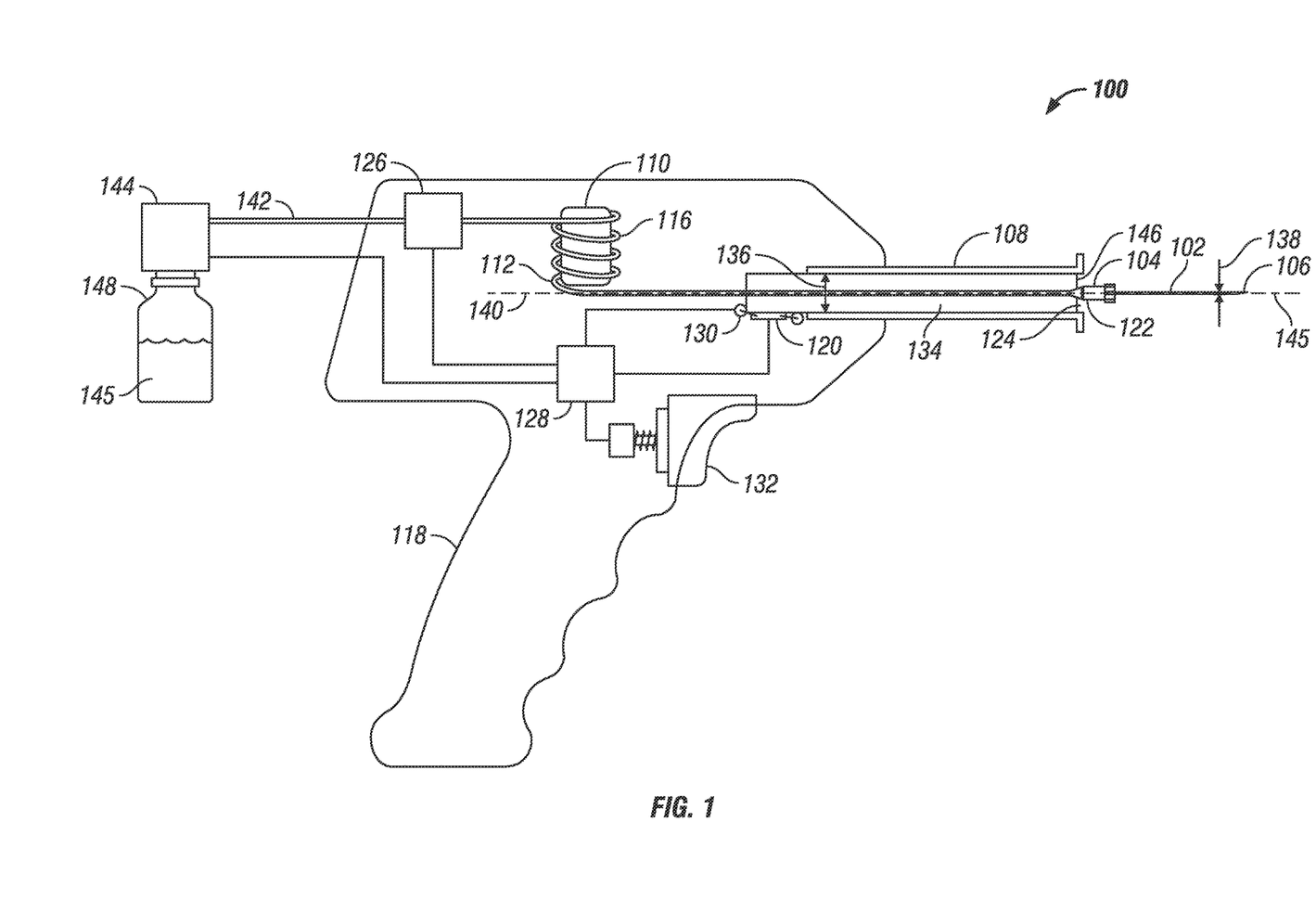
FIG. 1 illustrates an embodiment of the invention in its initial position.

Referring to FIG. 1, the distributed injection device 100 includes a needle 102, a housing 118 which includes a needle-receiving member 108, a therapeutic agent reservoir 110, a second reservoir 140, a reservoir-connecting conduit 142, a fluid drive 114, and a linear drive 120. Housing 118 may be constructed in any form capable of containing the necessary elements and providing ease of use, including in a pistol-grip style depicted in FIG. 1 or in the rod-grip style depicted in FIGS. 4 and 5.

Figure 2:
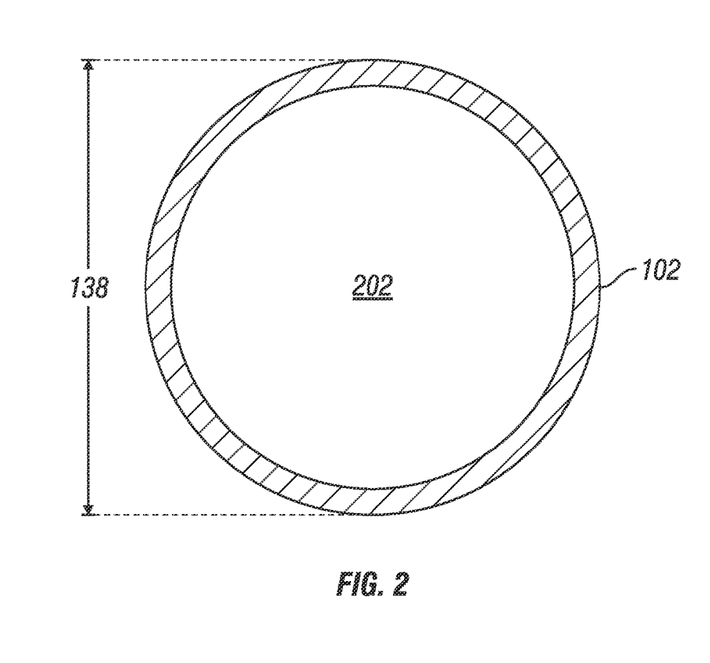
FIG. 2 illustrates the cross-sectional area of the needle of the present invention.

The needle 102 has an attachment end 104 and an injection end 106 and a needle outer diameter 138. This structure further defines the internal cross-sectional area 202 of the needle 102 (as depicted in FIG. 2) and defines the needle longitudinal axis 145 of the needle 102. The injection end 106 of the needle 102, as would be expected, may be sharpened to a prong to aid in penetration or may be flat if directed into a preexisting entry. Preferably, the needle 102 is affixed at its attachment end 104 to a slide member 134 at the slide member's first end 146 to reduce the length of needle needed for operation.

Constructed to ultimately surround the needle 102 after retraction and to provide shielding during retraction is a needle-receiving member 108. The needle-receiving member 108 is tubular and has an open first end 124 to communicate with the needle 102. As can be appreciated, to provide ease of retraction, the needle-receiving member 108 has a needle-receiving member inner diameter 136 greater than the needle outer diameter 138. Consistent with the retraction and shielding functions, the needle-receiving member 108 has a needle-receiving member longitudinal axis 148 generally parallel to the needle longitudinal axis and circumscribed within the needle-receiving member.

The therapeutic agent reservoir 110 is formed, constructed and adapted to contain a therapeutic agent 116 for delivery to the needle. Thus, the therapeutic agent reservoir 110 is in fluid communication with the needle 102 to facilitate the flow of the therapeutic agent 116 from the therapeutic agent reservoir 110 to the needle 102 and thereafter for injection in the body. Preferably, the therapeutic agent reservoir 110 is positioned within the housing 118 which is constructed to provide a safe barrier to the contents of the therapeutic agent 116, particularly where the therapeutic agent 116 may be radioactive. Ideally, the therapeutic agent reservoir 110 is created by a length of narrow tubing, preferably of cross-sectional area equivalent to the cross sectional area of the needle 102. The surface tension associated with the interior walls of the therapeutic agent reservoir 110 and its small cross-sectional area is ideally selected to ensure the therapeutic agent 116 exhibits near-capillary action. Thus, the therapeutic agent 116 can flow through the therapeutic agent reservoir 110 but maintains itself as a cohesive flow without mixing with any upstream flow.

A second reservoir 140 is adapted to contain a fluid 144, which may contain a therapeutic agent or which may, particularly where a radioactive agent is used, be a non-therapeutic agent, i.e. saline, intended to provide a fluid medium throughout in the system to provide a fluid drive against, including by application of a vacuum against, the therapeutic agent which is loaded through the needle, e.g. saline.

A reservoir-connecting conduit 142, preferably having an interior diameter equivalent to that of the therapeutic agent reservoir 110, is provided on the upstream side of the therapeutic agent reservoir 110 and is in communication with the therapeutic agent reservoir 110.

Intermediate the second reservoir 140 and the reservoir-connecting conduit 142, or otherwise positions to drive fluid from the second reservoir 140 to the reservoir-connecting conduit 142, is a fluid drive 114, such as a bidirectional pump (which may be a syringe in mechanical connection with a linear drive, in communication with the fluid 144 in the second reservoir 140 and in communication with the reservoir-connecting conduit 142. When engaged, the fluid drive 114 draws or directs fluid 144 from the second reservoir 140 and through the reservoir-connecting conduit 142. Because of the small cross-sectional area of the therapeutic agent reservoir 110, the fluid 144 from the second reservoir pushes the therapeutic agent 116 through therapeutic agent reservoir 110 without mixing. Moreover, due to the small cross-sectional area and the surface tension within the reservoir-connecting conduit 142 and the therapeutic agent reservoir 110, a bubble of air, if desired as a separator, may be introduced intermediate the fluid 144 and the therapeutic agent 116.

Figure 3:
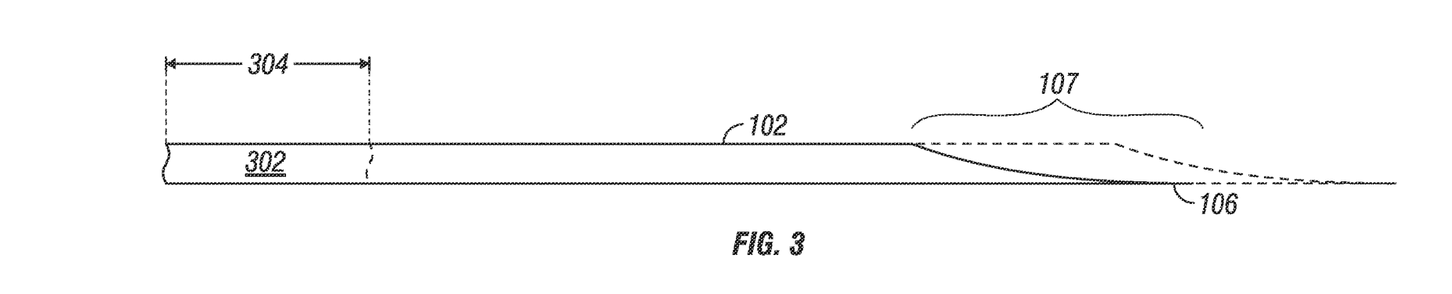
FIG. 3 illustrates the volume displacement of fluid during the displacement of the needle relative to the receiving member.
Figure 4:
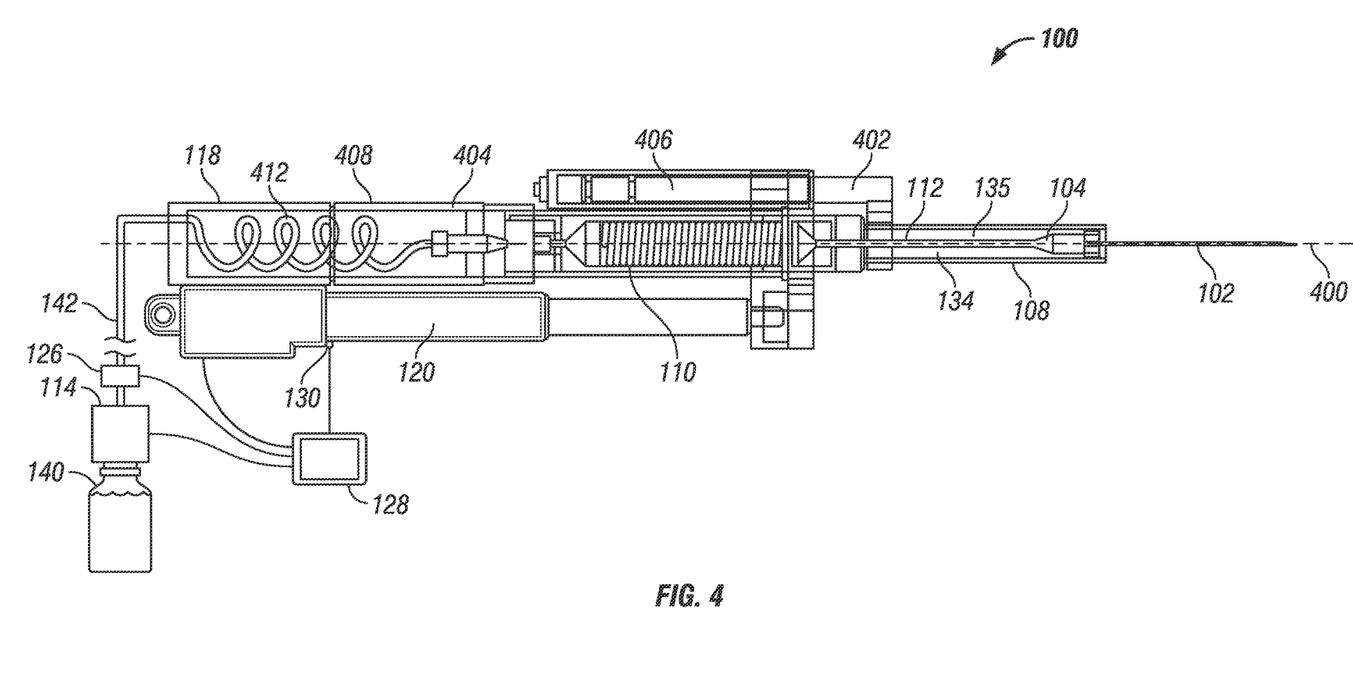
FIG. 4 illustrates an alternative embodiment of the invention in its initial position.
Figure 5:
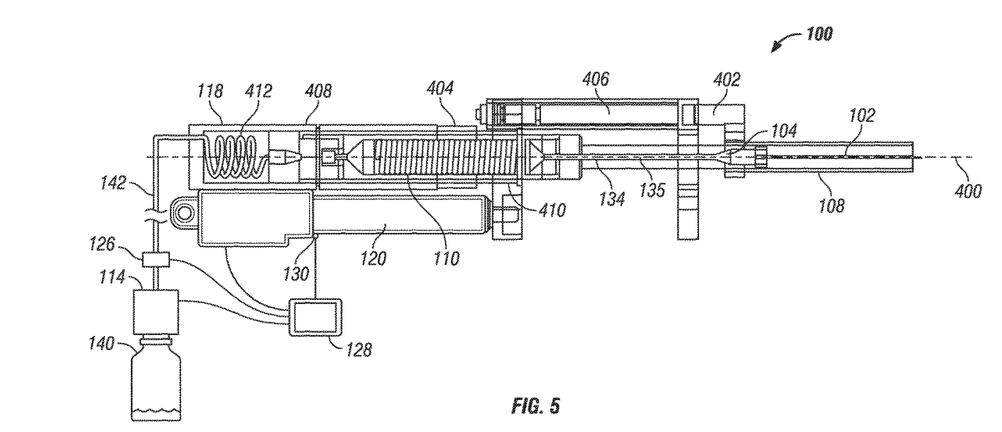
FIG. 5 illustrates the first alternative embodiment of the invention in its final position.

Finally, the device includes a linear drive 120 associated with the needle 102 or the needle-receiving member 108. During delivery of the therapeutic agent 116, pushed by the fluid 144 from the second reservoir 140 by fluid drive 114 through connecting conduit 142, the needle 102 is retracted from the body, preferably at a fixed or constant rate, although a control system may be used to vary the rate between depositions if a therapeutic agent is to be positioned at discrete locations throughout the body. As depicted in FIG. 3, the product of the displacement 304 of the needle 102 from the linear drive 120 and the internal cross-sectional area of the needle 102 provides the volume of displacement 302, and, in connection with the displacement per unit time, provides a flow rate. As a result of the structure, needle-retraction rate and flow rate form the fluid drive 114, the flow rate through the needle 102 is equal to the volume created per unit time for injection with the withdrawal of the needle 102 from the body. Thus, the therapeutic agent 116 may be delivered with low, even potentially zero, pressure differential. This pressure differential cannot be accurately achieved by human operation and ensures the therapeutic agent 116 is delivered exactly where desired and in the intended volume. Referring to FIG. 1, the linear drive 120 may be affixed to the needle 102, or may be affixed to a slide member 134 sized to slideably fit within the needle-receiving member 108, to provide a fitting for the needle 102 to ensure its rigid operation. The slide member 134 may include an internal passage 135 sized for the tubing 112, a part of the therapeutic agent reservoir 110, to pass through and connect directly to the needle 102 or may include an internal passage 135 having fittings at each end to connect to the needle 102 and the tubing 112 and thereby provide a conduit. The linear drive 120 may thereafter be fixed to housing 118 or the needle-receiving member 108 or other fixed components to ensure retraction of the needle 102 during operation, ultimately resulting in the repositioning of the needle 102 as depicted in FIGS. 4 and 5. Alternatively, the linear drive 120 may be affixed to the needle receiving member 108 to drive the needle-receiving member 108 towards the needle 102, resulting in encapsulating of the needle 102 while simultaneously repositioning the device 100 relative to the body, equivalent to the retraction of the needle 102, particularly helpful in providing immediate assessment of the extent of retraction of needle 102. The slide member 134 may also provide for a location for positioning of tubing 112 between the needle 102 and the therapeutic agent reservoir 110.

Referring to FIGS. 4 and 5, the rod-style grip, the distributed injection device 100 provides the needle 102, the needle receiving member 108, the therapeutic agent reservoir 110, and the linear drive 120 associated with the housing 118, and the second reservoir 140, and fluid drive 114 external the housing 118 and connected via the reservoir-connecting conduit 142. FIG. 4 depicts the rod-style grip of the distributed injection device 100 prior to and at the time of injection, whereby the needle 102 is at its most extended position. The alternative embodiment depicted in FIGS. 4 and 5 provides for the linear drive 120 to contract, thus repositioning the needle 102 into the needle receiving member 108 best described as retraction of the needle 102. FIG. 5 depicts the rod-style grip version of the distributed injection device 100 at the end of use, when the linear drive 120 is fully engaged (retracted) and the needle 102 is fully encapsulated.

As with the first embodiment, the needle 102 is affixed at its attachment end 104 to a slide member 134 which is repositioned within the needle-receiving member 108. All components in the rod-style grip are aligned with the longitudinal axis 400 of the distributed injection device 100.

The therapeutic agent reservoir 110 may be created by a length of narrow tubing as provided above, coiled about a portion of the slide member 134.

As depicted in FIGS. 4 and 5, the needle 102 is positioned at one end of the injection device 100 and is connected, preferably by the detachable fitting known in the art, to a slide member 134 having an internal passage 135 therethrough and which is connected to the therapeutic agent reservoir 110, the substantial length of which is coiled about the upper portion of the slide member 134. The receiving member 108 may be associated with a guide arm 402 extending from the upper portion 404 of the housing 118 to maintain position and alignment during operation. The guide arm 402 may extend a length equal to the stroke of the linear drive 120 to provide the retraction of the needle 102 while maintaining contact with the patient. To reduce binding, the guide arm 402 may telescope from a passage 406 and may, if desired, be loaded via a spring. The linear drive 120, which may be a piston-cylinder assembly, may be positioned opposite the slide member 134 from the guide arm 402 and may extend to drive the receiving member 108 forward and thus retract the needle 102. Thus, unlike the first embodiment where the linear drive 120 moves in the same direction as the needle 102, in the second embodiment the linear drive 120 moves relative to the needle 102 and therefore apparently in opposition.

Figure 6:
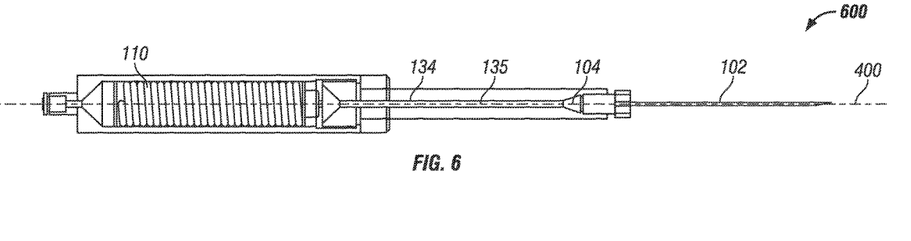
FIG. 6 illustrates a cartridge assembly which may be employed in the alternative embodiment.

Referring to FIGS. 4 and 5, and most particularly to FIG. 6, for ease of installation into the housing 118, the needle 102 and the therapeutic agent reservoir 110 may be incorporated into a single cartridge unit 600 for ease of installation and removal. Referring to FIGS. 4 and 5, the tubing 142 from the second reservoir 140 to the therapeutic agent reservoir 110 may include a coiled portion above the slide member 134, constructed to flex during operation of the linear drive 120 when the therapeutic agent reservoir 110, together with the slide member 134 travels downward.

The cartridge 600 is mounted in a telescoping tube receiver 408 which expands during initial operation of the linear drive 120 incident to retraction of the needle 102 from a body due to the advance of the needle-receiving member 108. The telescoping tube receiver 408 houses the end of a conduit 412 which is coiled to absorb the travel of the telescoping tube receiver 408. The telescoping tube receiver 408 is secured to the linear actuator via a mount block 410 which advances the telescoping tube receiver 408, causing it to telescopically extend. The coiled conduit 412 exits from the top of the telescoping tube receiver 408 and is connected to the conduit 142 from the second reservoir 140.

Beneficially, by locating within the housing 118 of the device 100 all those components which are in contact with the therapeutic agent 116 or irradiated by its energy, after use the therapeutic agent reservoir 110, the tubing 112, and the needle 102 may be removed for isolation and destruction and the housing 118, which may have provided shielding, placed in isolation or cleaned for subsequent use. Thus, a cartridge 600 may be generated. By locating the non-therapeutic units (second reservoir 140, fluid drive 114 and reservoir-connecting conduit 142) external of the housing 118, which is not necessarily required, these units do not need to be discarded or placed in isolation and can therefore be immediately used thereafter. This may be particularly helpful if the volume of therapeutic agent reservoir 110 provides less volume of therapeutic agent 116 than needed during an operating session. Alternatively, all components can be located within the housing 118 to provide a self-contained device. However, all components will thereafter be subject to post-use restrictions and potential isolation, requiring disposal of the fluid 144 consistent with more stringent requirements.

To the extent the therapeutic fluid 116 contains radioisotopes, the housing 118 and the receiving member 108 may be constructed of or coated with a shielding material to protect the operator from radiation emitted from the needle 102 where the fluid 116 is radioactive. In the preferred embodiment, receiving member 108 is constructed of tungsten. The therapeutic agent reservoir 110 may also be constructed of or coated with a shielding material to protect the operator in such an instance. For example, if a radioisotope is selected who energy is unable to pass through plastic, then the components may include a plastic layer or may be composed of plastic.

In one embodiment, as illustrated in FIG. 1, a flow meter 126 may be positioned intermediate the second reservoir 140 and the needle 102 and may provide data to a computer 128 to compare with data from a linear positioning sensor 130 to ensure the flow rate from the therapeutic agent reservoir 110 is equal to the flow rate associated with the retraction of the needle 102 through the body.

The housing 118 may include an operating switch 132 which permits the operator to simultaneously activate the linear drive 120 and the fluid drive 114 to ensure the deposition of fluid 116 at the injection end 106 of the needle 102 along the path of needle 102 during retraction. Alternatively, the operating switch 132 may control only the linear drive 120 and may provide for manual advancement, for manual retraction and for computer engagement, and may even be two or three separate buttons, whether a separate button for each function or each of two buttons for manual operation with computer engagement activated by depressing both buttons simultaneously.

After use, the needle 102, the therapeutic agent reservoir 110 and any tubing 112 may be removed from the housing 118 for disposal in compliance with safety regulations and the balance of the components not contacting the fluid 116 used again.

In operation as illustrated in FIGS. 7A and 7B, in a first step 702, the distributed injection device 100 is positioned in a first position, in which the needle 102 is fully extended from the housing 118, and the slide member 134 is fully extended into the needle-received member 108, as illustrated in FIG. 4. This may be accomplished via the computer 128. The linear-position sensor 130 may be used to confirm positions to the computer 128.

In a second step 704, the connecting conduit 142, the therapeutic agent reservoir 110 including the tubing 112, and the needle 102 are fully filled with the fluid 144 of the second reservoir 140. This may be controlled by the computer 128, by operation of the fluid drive 114 for an allocated time at allocated speed. Alternatively, or in addition, the flow meter 126 may be used to control or verify the extent of pumping of the fluid 144. At step 706, the operator determines whether a therapeutic agent is included in the fluid 144, or not. If the therapeutic agent is included in the fluid 144, the method proceeds to step 714. If the therapeutic agent is not included in the fluid 144, the method proceeds to step 708. This second option may be advantageous where a radioactive therapeutic agent is used, or where a therapeutic agent is available or is desired to be used in limited volumes.

In step 708, the volume of fluid 144 in the needle 102 is reduced sufficient to generate an air pocket proximate the injection end 106 of the needle 102, and beyond the piercing portion 107 of the needle 102. Step 708 is accomplished by the computer 128 reversing the direction of operation of the fluid drive 114, selected for bidirectional operation, sufficient to withdraw enough fluid to generate the air pocket. The flow meter 126 may be used to confirm the volume of fluid 114 withdrawn.

In step 710, the distributed injection device 100 is brought into contact with the therapeutic agent. The injection end 106 of the needle 102 is placed in fluid communication with the therapeutic agent and, as applicable, is carrier. If the therapeutic agent is radioactive, the injection end 106 of the needle 102 may be placed in a pig—a container, usually of lead or depleted uranium used to store radioactive materials. Similarly, if the therapeutic agent is not radioactive, but is limited in volume, the injection end 106 of the needle 102 may be placed in the therapeutic agent-containing vial or container.

In step 712, the computer 128 causes the therapeutic agent to fill the therapeutic agent reservoir 110 of the distributed injection device 100. The computer 128 activates the fluid drive 114 in a reverse flow direction, withdrawing fluid 144 from the distributed injection device 110, necessarily withdrawing first from the needle 102, forming a vacuum against the therapeutic agent, which is drawn into the needle 102, then into the tubing 112 and into the balance of the therapeutic agent reservoir 110. The flow meter 126 may be used to confirm the volume of fluid 114 withdrawn and therefore the volume of therapeutic agent drawn into the distributed injection device 100. The therapeutic agent reservoir 110 is therefore fully-filled, and operationally identical to the filling of the entire distributed injection device 100 from the second reservoir 140.

Figure 7A:
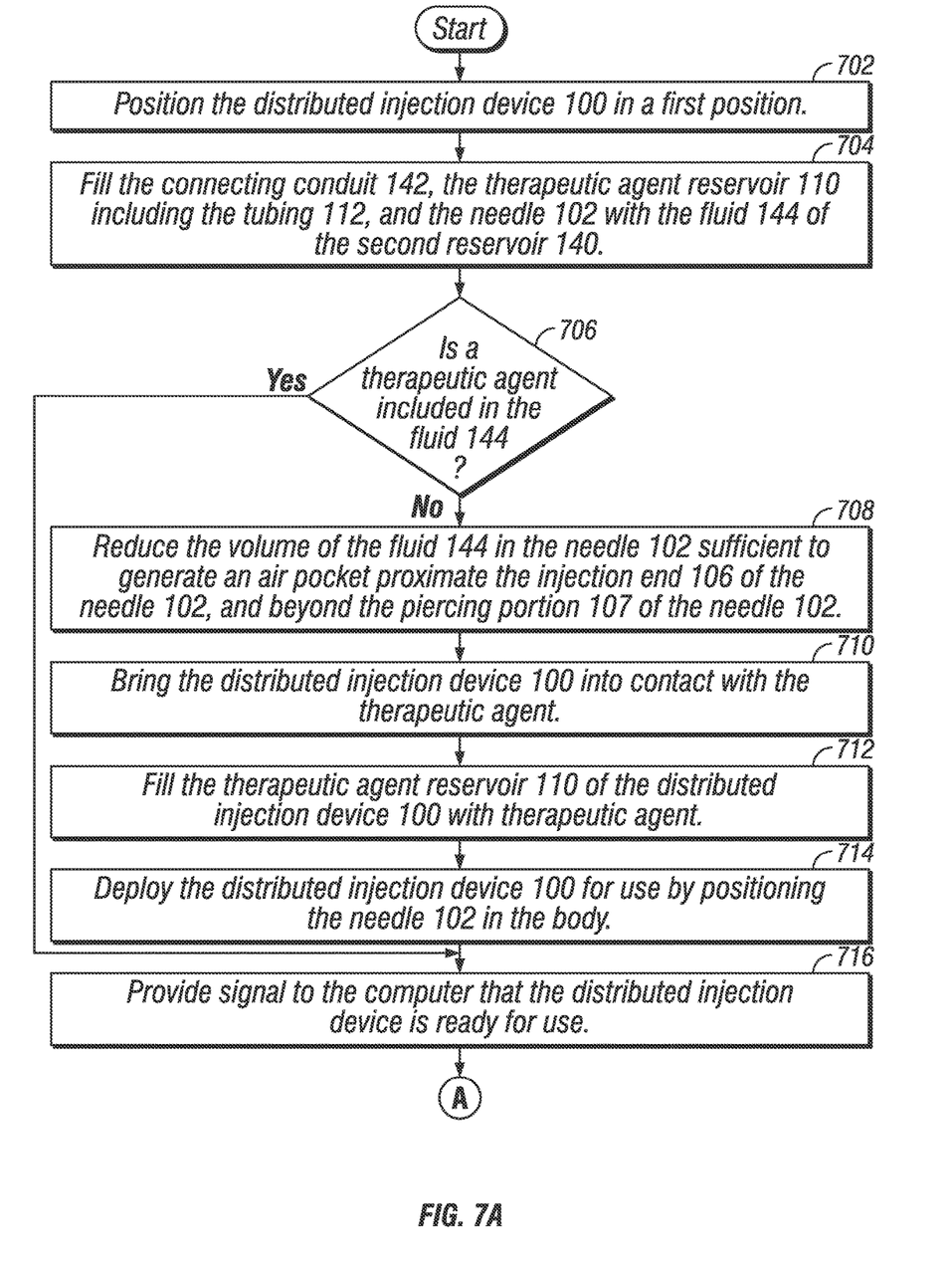
FIGS. 7A and 7B illustrate one method of operation of the present invention.

In step 714, the distributed injection device 100 is deployed for use. The needle 102 is positioned in the body, whether by being driven into the tissue, or by being driven to an end point of a prepared passageway. This positioning may be accomplished manually, or by an armature controlled by another computer.

In step 716, the computer 128 is provided input that the distributed injection device is ready for use. This may be accomplished by a user input, or by a signal from another computer.

In step 718, the computer 128 determines whether the therapeutic agent is to be dispensed as a continuous path or as a series of separated locations. This may be accomplished by a user input or a default setting. If the therapeutic agent is to be dispensed as a continuous path, the method proceeds to step 720. Otherwise, the method proceeds to step 722.

In step 720, the therapeutic agent is introduced throughout a zone of the body as a continuous path. The computer 128 causes the linear drive 120 to cause the needle 102 to be retracted from the body while fluid 144 is driven into the connecting conduit 142 by the fluid drive 114, and then, as necessary, into the therapeutic agent reservoir 110, the tubing 112 and the needle 102, dispensing the therapeutic agent. Preferably, the fluid drive impels fluid 144 from the second reservoir 140 into the reservoir-connecting conduit 142 and thus drives the therapeutic agent from the therapeutic agent reservoir 110 at a flow rate consistent with the linear displacement of the needle 102 towards the housing 118. Notably the fluid communication from the therapeutic agent reservoir 110 to the needle 102 is maintained by the tubing 112 during operation of the linear drive 120 to provide a linear displacement of the needle 102 towards the housing 118, or to provide a linear displacement of the needle-receiving member 108 away from the housing 118. The computer 128 and linear drive 120 cause the needle 102 to be fully retracted into the needle receiving member 108, at which point, or before, the injection is fully completed and the method completed.

Figure 7B:
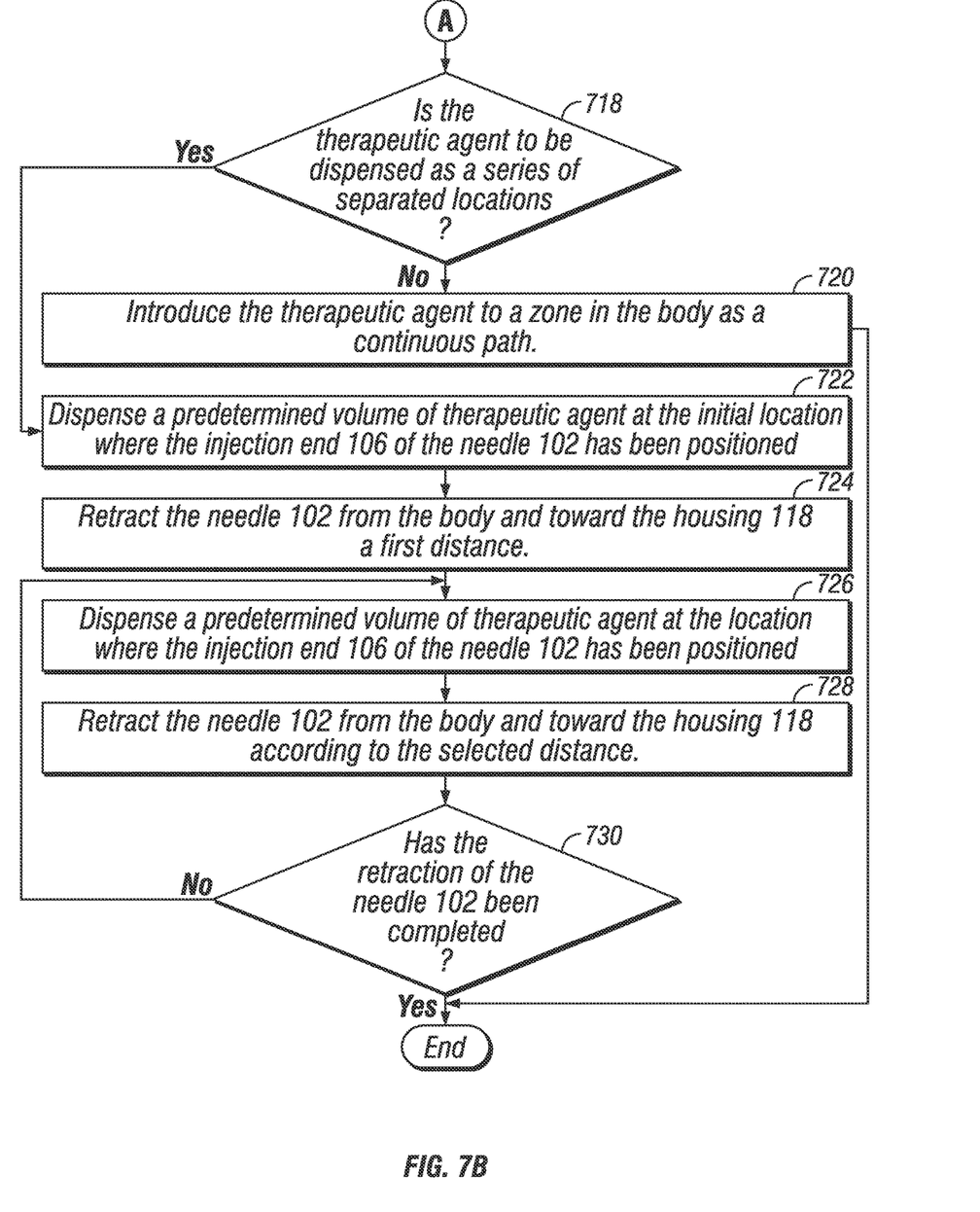

In step 722, the method begins distributing the therapeutic agent throughout a zone of the body as a series of separated locations. The computer 128 first causes the fluid drive 114 to dispense a predetermined volume of therapeutic agent at the initial location where the injection end 106 of the needle 102 has been positioned.

In step 724, the computer 128, via the linear drive 120, causes the needle 102 to be retracted from the body and toward the housing 118 a first distance. While a user-defined distance or be a default distance may be selected for the distance between injections along the path, the distance on the first retraction may be less than the selected to ensure the final injection is the selected distance from the outer layer of skin.

In step 726, the method causes the fluid drive 114 to dispense the predetermined volume of therapeutic agent at the location where the injection end 106 of the needle 102 has been positioned.

In step 728, the computer 128, via the linear drive 120, causes the needle 102 to be retracted from the body and toward the housing 118 according to the selected distance.

In step 730, the computer 128 determines if the retraction of the needle 102 is completed. If the needle 102 is not fully retracted into the needle receiving member 108, the method returns to step 726. If the needle 102 has been fully retracted into the needle receiving member 108, as depicted in FIG. 5, the injection is fully completed and the method completed.

The present invention provides significant advantages over the prior art. When high pH radioisotopes are used in treating illness, it is undesirable for the radioisotope to mix with the blood. Rather, it is desirable to deposit the radioisotope along a line in the tissue, either as a continuous path or as a series of separated locations, particularly along the path of the needle 102 through the body tissue. It appears the high pH radioisotope typically reacts with the tissue, causing coagulation of the microcapillaries and precluding entry of the radioisotope into the bloodstream. Injection of the total volume of the liquid, however, does cause undesirable loss of the radioisotope into the bloodstream. Ideally, a plurality of injection lines are utilized, as the range of the radioisotope is quite small, often in the range of six (6) millimeters (mm) on each side of the injection line. A plurality of injection lines, each corresponding to the needle path, therefore, blankets the tumor, with a substantial portion, potentially nearing ninety percent (90%) of the radioisotope remaining in the tumor and being effective there, with only a de minimus portion entering the remainder of the body, in quantities sufficiently low to pose a substantially lower risk of injury that current methods.

Various alternatives and/or modifications may be made to the disclosed embodiments without departing from the spirit or scope of the invention.

We claim:

1. A distributed injection device, comprising
a needle, said needle having an attachment end and an injection end, said needle having a needle outer diameter, and said needle having an internal cross-sectional area, said needle having a needle longitudinal axis;
a housing including a needle-receiving member, said needle-receiving member being tubular, said needle-receiving member having an open first end, said needle-receiving member having a needle-receiving member inner diameter, said needle-receiving member inner diameter greater than said needle outer diameter, said needle-receiving member having a needle-receiving member longitudinal axis, said needle longitudinal axis and said needle-receiving member longitudinal axis generally parallel, said needle-receiving member circumscribing said needle longitudinal axis;
a reservoir adapted to contain a therapeutic agent, said therapeutic agent reservoir in fluid communication with said needle via a tubing, said therapeutic agent reservoir positioned within said housing;
a second reservoir adapted to contain fluid;
a reservoir-connecting conduit, said reservoir-connecting conduit in communication with said therapeutic agent reservoir;
a bidirectional fluid drive in communication with said fluid in said second reservoir, said bidirectional fluid drive in communication with said reservoir-connecting conduit; and
a linear drive associated with said needle or said needle-receiving member;
said linear drive adapted to provide a linear displacement of said needle towards said housing, or to provide a linear displacement of said needle-receiving member away from said housing;

a computer in communication with said bidirectional fluid drive and with said linear drive;

wherein said bidirectional fluid drive adapted to impel fluid from said second reservoir to said reservoir-connecting conduit and to drive said therapeutic agent from said therapeutic agent reservoir after said linear displacement of said needle towards said housing; and wherein said fluid communication from said therapeutic agent reservoir to said needle is maintained by said tubing during operation of said linear drive to provide a linear displacement of said needle towards said housing, or to provide a linear displacement of said needle-receiving member away from said housing.

2. The distributed injection device of claim 1 further comprising a slide member, said needle fixed in position at a first end of said slide member, said slide member slidably positioned within said receiving member; and said linear drive connected to said slide member.

\* \* \* \* \*